(12) United States Patent
Bellussi et al.

(10) Patent No.: US 8,409,823 B2
(45) Date of Patent: Apr. 2, 2013

(54) INTEGRATED PROCESS FOR THE PRODUCTION OF BIO-OIL FROM MICRO-ORGANISMS

(75) Inventors: Giuseppe Bellussi, Piacenza (IT); Giacomo Rispoli, Rome (IT); Aldo Bosetti, Vercelli (IT); Daniele Bianchi, Arese (IT); Giuseppe Gioventu, Pavia (IT)

(73) Assignee: ENI S.p.A., Rome (IT)

( * ) Notice: Subject to any disclaimer, the term of this patent is extended or adjusted under 35 U.S.C. 154(b) by 48 days.

(21) Appl. No.: 13/125,695

(22) PCT Filed: Oct. 16, 2009

(86) PCT No.: PCT/EP2009/007582
§ 371 (c)(1),
(2), (4) Date: Aug. 18, 2011

(87) PCT Pub. No.: WO2010/046115
PCT Pub. Date: Apr. 29, 2010

(65) Prior Publication Data
US 2011/0294175 A1    Dec. 1, 2011

(30) Foreign Application Priority Data
Oct. 23, 2008    (IT) .............................. MI2008A1873

(51) Int. Cl.
*C12P 39/00*    (2006.01)
(52) U.S. Cl. ......................................................... 435/42
(58) Field of Classification Search ...................... 435/42
See application file for complete search history.

(56) References Cited

U.S. PATENT DOCUMENTS

2008/0090284 A1    4/2008    Hazlebeck et al.
2009/0298159 A1    12/2009   Wu et al.

FOREIGN PATENT DOCUMENTS

| CN | 101 280 328 | 10/2008 |
|----|-------------|---------|
| WO | 2010 014797 | 2/2010  |

OTHER PUBLICATIONS

U.S. Appl. No. 13/395,028, filed Mar. 8, 2012, Bosetti, et al.

Xu, H., et al., "High quality biodiesel production from a microalga *Chlorella prototheocoides* by heterotrophic growth in fermenters," Journal of Biotechnology, vol. 126, pp. 499-507, (2006) XP 0024956582.

Li, X., et al., "Large-Scale Biodiesel Production From Microalga *Chlorella protothecoides* Through Heterotrophic Cultivation in Bioreactors," Biotechnology and Bioengineering, vol. 98, No. 4, pp. 764-771, (Nov. 1, 2007) XP 002546299.

Chen, F., "High cell density culture of microalgae in heterotrophic growth," Trends in Biotechnology, vol. 14, pp. 421-426, (Nov. 1996) XP 004069639.

Huntley, M.E., et al., "$CO_2$ Mitigation and Renewable Oil Form Photosynthetic Microbes: A New Appraisal," Mitigation and Adaptation Strategies for Global Change, vol. 12, pp. 573-608, (2006) XP 0019506383.

International Search Report issued May 17, 2010 in PCT/EP09/007582 filed Oct. 16, 2009.

*Primary Examiner* — Maryam Monshipouri
(74) *Attorney, Agent, or Firm* — Oblon, Spivak, McClelland, Maier & Neustadt, L.L.P.

(57) ABSTRACT

The cultivation of heterotrophic and phototrophic micro-organisms is integrated for the production of bio-oil for biofuels, wherein the overall algal suspension produced is first thickened, with recirculation of the excess water to cultivation containers, and then thermally treated at a high temperature. After cooling, a bio-oil phase is recovered together with a suspension rich in soluble carbohydrates and proteins which forms a nutritional/energy source for heterotrophic microorganisms.

20 Claims, 1 Drawing Sheet

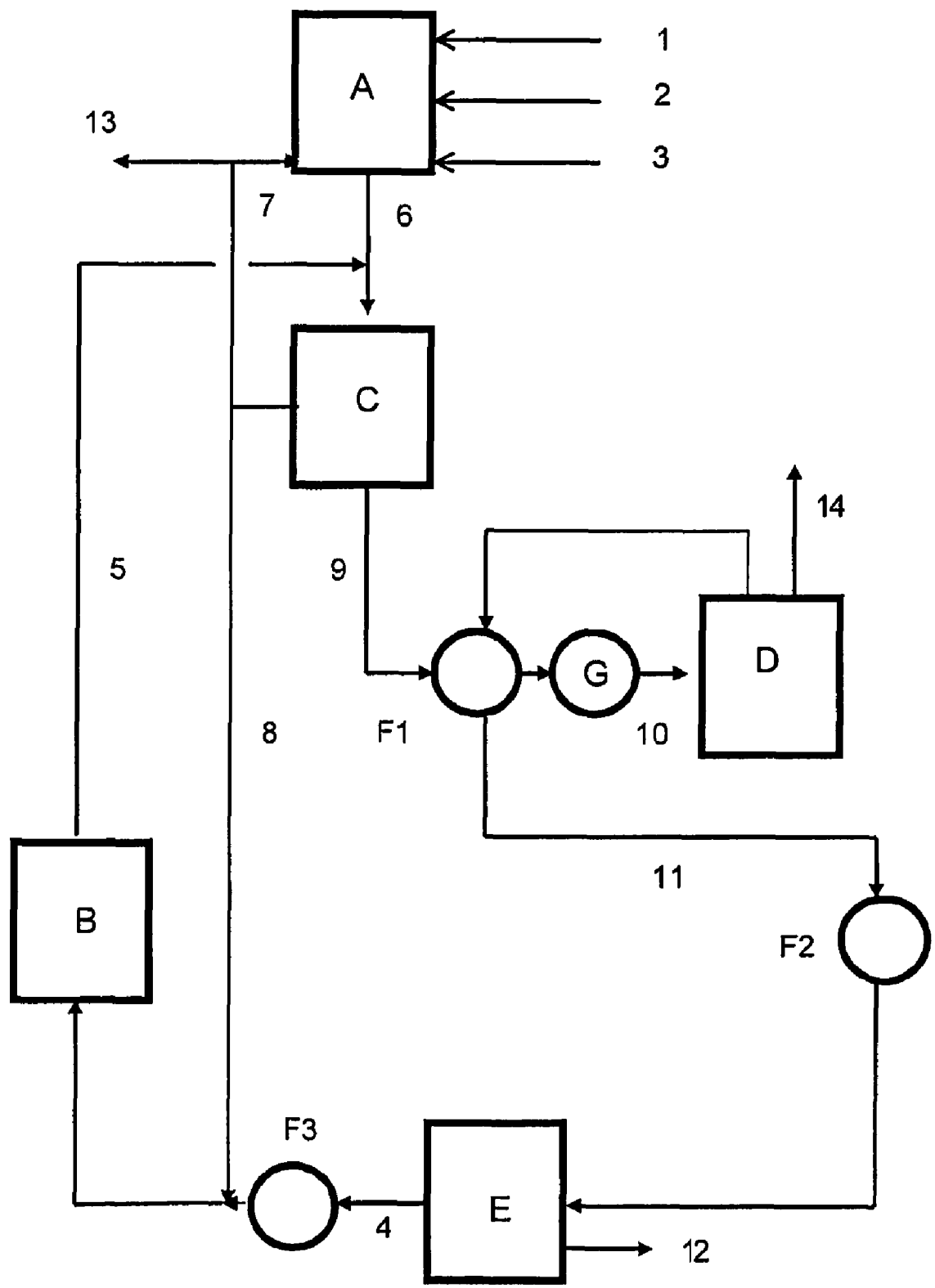

INTEGRATED PROCESS FOR THE PRODUCTION OF BIO-OIL FROM MICRO-ORGANISMS

This application is a 371 of PCT/EP2009/007582, filed Oct. 16, 2009, which claims foreign priority to Italian application MI2008A 001873, filed Oct. 23, 2008.

The present invention relates to an integrated process for the production of bio-oil from micro-organisms, single or in a consortium.

More specifically, the present invention relates to a process for the production of bio-oil, for biofuels, from biomasses of a microbial origin obtained by integrating a cultivation of phototrophic microalgae with a cultivation of heterotrophic micro-organisms. The biomasses can also be obtained by means of cultivation schemes which include the cooperative use of various microbial forms, of the autotrophic or phototrophic type, for synthesizing the biomass with the use of $CO_2$ and solar light, and of the heterotrophic type, which grows in the absence of light, using carbohydrates as energy/nutrition source for producing the biomass.

Even more specifically, the present invention relates to a process integration based on a method for the cultivation of microalgae, phototrophs and heterotrophs, suitable for being used in the production of biomasses, preferably in a consortium with micro-organisms, using $CO_2$, coming from generic combustion plants and/or decarbonization plants of gaseous streams, and generic water, both fresh and salty, in addition to nutriments based on phosphorous, nitrogen and oligo-elements.

Studies for the growth of microalgae are known, see for example W. J. Oswald, "Journal of Applied Phycology" 15, 99-106, 2003. The existence of different species of microalgae capable of growing in high salinity environments, for example higher than that of the sea, is also known. Cultivations of microalgae generally use fresh or salt water to which nutrients and mineral salts and, when necessary, vitamins have been added, and are effected in bioreactors and/or large-sized ponds, for example from 5 to 100 m long and from 1 to 100 m wide, with a depth ranging from 0.2 to 2 m, possibly under solar irradiation. Carbon dioxide, stored, in liquid or gaseous form, in specific ponds or recovered from exhausted gases of industrial processing, for example from methane/coal electric power stations, decarbonization plants of natural gas or other fuel gases (for example, hydrogen) possibly diluted with air, can also be fed to the ponds together with water. In order to have the maximum availability of $CO_2$ for microalgae, the gaseous phase is bubbled through the liquid mass using perforated ducts immersed in the growth pond.

The cultivation of microalgae requires few essential components comprising, in addition to an energy/nutritional source, consisting of light and $CO_2$ and/or carbohydrates and proteins, also, as mentioned above, salts and substances based on nitrogen, phosphorous and oligo-elements.

The biomass obtained from microalgae, cultivated so as to maximize their lipid content, suitably extracted, can be used as raw material for bio-oil to be fed to industrial plants for the production of biofuels. The bio-oil produced from microalgae, therefore offers the advantage of not being in competition with crops for nutritional use.

Both phototrophic and heterotrophic microalgae, alone or in a consortium with other micro-organisms, are capable of growing in both fresh water and water having a high salinity, for example brackish water, with a concentration of salts even higher than 5 g/l. In natural ecosystems, microalgae often coexist with other micro-organisms (other algae and bacteria, for example) with which they develop interactions which increase the stability and survival of the consortium.

The term "microalgae", as used in the present description and claims, refers, also when not specified, to vegetal microorganisms and phototrophic prokaryotes alone or consortia of micro-organisms, natural or specifically cultivated, which contain the same microalgae.

The production of bio-oil from microalgae is advantageous with respect to cultivation from agricultural crops as it allows a greater production of oil per hectare of surface per year. Microalgae which can be used for the production of bio-oil can be of the phototrophic type which use solar light and $CO_2$ as energy source, or of the heterotrophic type which use a carbon source, such as carbohydrates and/or proteins, in the absence of light.

A disadvantage of phototrophic microalgae is that they grow with a low density. As the aqueous suspension becomes more opaque and therefore less transparent to light, with an increase in the concentration of the algal mass, in fact, the growth diminishes until it stops above a certain concentration. The necessity of favouring the penetration of light also limits the maximum depth of the ponds to a few tens of centimeters.

The low concentration of the algal mass, per liter of aqueous suspension, and the low depth of the ponds involve the use of large volumes of water and relatively extensive surfaces and therefore high costs and energy consumptions for the separation and extraction of the bio-oil or, alternatively, relatively low productive yields to bio-oil.

Heterotrophic microalgae, also in consortium with other micro-organisms, do not use light for the production of algal biomass and consequently their concentration in the aqueous medium does not suffer from the light penetration limit in the growth medium. As they grow in the dark, on the other hand, they require an energy and carbon source alternative to light and $CO_2$. This source is based on carbohydrates and possibly proteins, not always easily available at competitive costs.

The Applicant has now found a process for the production of bio-oil from algal masses, to be used for the production of biofuels, which is able to combine the advantages of both phototrophic and heterotrophic micro-organism production, overcoming the relative disadvantages. The present invention is based on the principle according to which phototrophic microalgae produce an algal biomass, using light and carbon dioxide, from which bio-oil can be separated together with an aqueous suspension consisting of polysaccharides and protein aggregates. For the extraction of the bio-oil, the biomass is conveniently subjected to a hydrothermal treatment which promotes the separation of the oil phase and the transformation of the polysaccharides and protein aggregates into carbohydrates and simple proteins, which can be more easily used for feeding and growing biomass from heterotrophic microalgae, which are also producers of bio-oil.

As heterotrophic microalgae can reach very high concentrations in the growth water, with the present invention, it is possible to produce bio-oil from microalgae using a much lower overall quantity of water than that which would be used with the cultivation of phototrophic microalgae alone. A second advantage of the present invention is that it requires a lower cultivation surface with respect to the use of phototrophic microalgae alone with the same production of bio-oil.

An object of the present invention therefore relates to an integrated process for the production of bio-oil from micro-organisms, both phototrophic and heterotrophic, which comprises:

a. growing at least one phototrophic microalga, possibly in consortium with other micro-organisms, in specific ponds/ containers containing water and nutrients and a device suitable for distributing carbon dioxide in the form of micro-bubbles in the water mass;

b. growing at least one heterotrophic microalga, possibly in consortium with other micro-organisms, in specific ponds/containers containing water and nutrients in the presence of carbohydrates and/or proteins transported by a suspension coming from a hydrothermal treatment of a biomass;

c. recovering the biomass developed (at the end of the growth), obtained from phototrophic and heterotrophic cultures, with its growth water, and subjecting the overall suspension thus obtained to thickening, up to at least 5% by weight, in a specific section;

d. subjecting the thickened suspension to thermal treatment, at a temperature ranging from 80 to 350° C. and a pressure of 0.1 to 25 MPa, for a time greater than or equal to 1 minute;

e. recovering, after cooling the thickened thermally treated suspension, an oil fraction sent to treatment suitable for producing biofuels, for example hydrogenation and/or transesterification treatment; and f. feeding the remaining aqueous suspension, rich in hydrosoluble carbohydrates and proteins assimilable by heterotrophic microalgae, to step (b).

According to the present invention, the phototrophic and heterotrophic micro-organisms are cultivated in ponds/containers having large dimensions, for example from 5 to 100 m in length and from 1 to 100 m in width, with depths greater than 0.2 m and preferably ranging from 0.5 to 10 m, maintained under solar irradiation, necessary for phototrophic microalgae, or in the dark, by means of appropriate covers, necessary for heterotrophic microalgae. Alternatively, the heterotrophic microalgae are grown in closed containers.

In the case of phototrophic microalgae, photo-bioreactors can also be used.

The water necessary for the growth of the microalgae, of both species, can be fresh water or salt water coming from natural or artificial sources, for example from industrial processings.

Examples of phototrophic microalgae can be selected from types such as *Tetraselmis, Nannochloropsys, Scenedesmus, Ankistrodesmus, Phaeodactylum, Chlorella, Amphipleura, Amphora, Chaetoceros, Cyclotella, Cymbella, Fragilaria, Navicula, Nitzschia, Achnantes, Dunaliella, Oscillatoria, Porphiridium* or combinations thereof.

Examples of heterotrophic microalgae can be selected from *Chlorella, Nannochloropsys, Nitzschia, Thraustochytrium* or combinations thereof, possibly in consortium with bacteria such as, for example, strains belonging to the species alpha-*Proteobacteria*, beta-*Protobacteria*, *Actinobacteria, Firmicutes, Flavobacteria-Cytophaga*.

The salt water can be seawater or of the brackish type, either natural or artificial, also with a saline concentration, for example ranging from 5 to 350 g/liter. An example of brackish water, which can be used in the process, object of the present invention, is water coming from oil production fields.

In particular, the oil production fields in the North-African region are situated in a context with high solar irradiation, in desert areas which cannot be used for food crops and have a high coproduction of water which generally has a volume several times higher than the corresponding oil production.

If necessary, it is possible to favour algal growth, or the growth of the algal consortium, by feeding nutrients based on carbohydrates, proteins, nitrogen, phosphorous, oligo-elements, etc., when these are not already present in water. In general, solutions of various types of carbohydrates are fed such as, for example, acetate, glucose, glycine to favour growth in heterotrophy, in addition to organic and/or inorganic salts soluble in water, such as for example, ammonium salts and phosphates of alkaline or alkaline earth metals, for example sodium, potassium, calcium, magnesium phosphates, or ammonium phosphates. Finally, in the case of phototrophic microalgae, a stream of carbon dioxide, as carbon source, is fed to the water, in addition to the salts of N and P and oligo-elements, through specific distributors which are deposited on the bottom of the cultivation ponds or suitably inserted in the growth containers (photo-bioreactors).

When the micro-organisms, both phototrophic or heterotrophic, reach maturity, they are discharged from the growth ponds/containers together with the growth water and sent to a thickening phase. In this phase, the concentration of the algal suspension is brought to values ranging from 5 to 30% by weight, preferably from 18 to 25% by weight, by means of techniques such as sedimentation, decanting, flocculation, filtration, etc. The excess water is recycled to the ponds/containers of both the phototrophic microalgae and heterotrophic microalgae, whereas the concentrated suspension is fed to a hydrothermal treatment for the production of bio-oil and an aqueous solution of nutrients.

The thermal treatment (hydrothermal treatment) comprises heating the suspension of concentrated biomass in a container, under pressure, to a temperature ranging from 80 to 350° C., preferably from 150 to 330° C. The pressure is maintained at such values as to keep at least part of the water in the liquid state. The pressure can be maintained, for example, at between 0.1 and 25 MPa, preferably from 0.5 to 18 MPa.

Considering that the thermal energy necessary for the thermal treatment can derive from the combustion of traditional energy vectors, for example methane gas, LPG, mineral oil, coal, etc. it is not excluded that the thermal energy can derive from solar energy and/or Solar Pond, above all in desert areas close to equatorial regions.

During the thermal or hydrothermal treatment phase, the breakage of the cell membranes and separation of the oil phase are effected. Furthermore, the polysaccharides and protein material are partially converted to bio-oil whereas the remaining part is hydrolyzed producing glucoside and protein fractions soluble in water and easily assimilable as nutrition by both heterotrophic microalgae and micro-organisms which live with them in consortium. Consequently, at the end of the thermal treatment, which has a duration equal to or higher than 1 minute, for example from 0.5 to 2 hours, the residual biomass is cooled to a temperature ranging from 45 to 80° C. and fed to a separation/recovery section of the bio-oil, by means of known techniques and devices such as, for example, a static separator.

The aqueous suspension separated is possibly further cooled to a temperature ranging from room temperature to 50° C. and sent to the cultivation section of the heterotrophic micro-organisms.

During the thermal treatment, a gaseous phase is also formed equal to about 10-25% by weight of the biomass (referring to the dry product) subjected to thermal treatment and essentially consisting of carbon dioxide, for example about 80-90% by volume, and $C_1$-$C_3$ hydrocarbons, for the remaining 10-20%. This gaseous phase is preferably separated, during the recovery phase of the bio-oil, and used as supplementary source of carbon dioxide for the growth of the phototrophic microalgae and upgraded in its hydrocarbon component as fuel gas.

At the end of the growth of the heterotrophic microalgae, possibly in a consortium, the latter are discharged from the cultivation ponds/containers, with the growth water, and the whole mixture is combined with the flow coming from the cultivation of phototrophic microalgae to be thickened.

BRIEF DESCRIPTION OF THE DRAWING

FIG. 1 is a schematic diagram showing an embodiment of the integrated process of the present invention. This FIGURE is included for illustrative and non-limiting purposes.

According to the enclosed scheme, A represents the cultivation ponds/containers of the phototrophic microalgae and B the cultivation ponds/containers of the heterotrophic microalgae. C represents a thickening section of the suspension comprising the algal mass, produced both in A and B, and the recycled aqueous suspension.

D is a pressurized container, E is a separator, F1, F2 and F3 are heat exchange sections and G (in bold) is a heat generator.

The cultivation ponds A produce a phototrophic microalga, which grows for example in seawater. Make-up water, $CO_2$ and nutrients, for example soluble ammonium and phosphorous salts, reach these ponds, through lines (1), (2) and (3) respectively.

In the same way, the containers B produce a heterotrophic microalga, which also grows in seawater. An aqueous suspension, rich in carbohydrates and/or proteins soluble in water, a residue of the hydrothermal treatment in D, reach the containers B, through line 4.

When the microalgae, both phototrophic and heterotrophic, reach maturity, they are collected by completely or partially emptying the respective cultivation containers and sent, through lines (5) and (6), to a thickening area C where they are concentrated to give a suspension, for example 20% by weight. The excess water is recycled to the containers A and B through lines (7) and (8) respectively.

The thickened suspension (9) is preheated in F1, possibly brought to temperature in G, then fed to the pressurized container D, through (10). In D, the suspension is brought to the temperature and pressure conditions and residence times which allow a bio-oil to be obtained, which is suitable for being transformed into biofuel, and producing an optimum aqueous phase for its subsequent use as a source of nutrients/energy for the growth of heterotrophic micro-organisms. During the thermal treatment, a gaseous phase (14), essentially consisting of $CO_2$ and $C_1$-$C_3$ gaseous hydrocarbons, is produced, which can be recycled to the system or sent to treatment sections.

For this reason, the residual degraded algal mass is discharged from the container D, through (11), and the whole mixture (residual mass+suspension water) is cooled in F1 and subsequently in F2. The bio-oil is then recovered in the separator E, which can be sent, by means of (12), to the subsequent processing phases to transform it into biofuel by means of treatment, for example hydrogenation and/or esterification (not illustrated in FIG. 1), whereas the residual aqueous suspension, rich in hydrosoluble carbohydrates and proteins, is fed, after possible further cooling in F3 and through (4), to the cultivation containers B of the heterotrophic microalgae.

As the production cycle is subject to the possible accumulation of salts and organic substances, a purging (13) can be envisaged, which allows the levels of these products to be kept within the management limits of the production plant.

Again for illustrative and non-limiting purposes, an applicative example is provided hereunder.

EXAMPLE

Cultivation ponds with seawater are used, with a total surface, for phototrophic microalgae, of about 377 hectares, 30 cm deep.

The phototrophic microalga is *Nannochloropsys*.

Cultivation ponds with seawater with a total surface area, for heterotrophic microalgae, of about 8 hectares, 1 m deep, are used.

The heterotrophic microalga is a heterotrophic strain belonging to the genus *Nannochloropsys*.

The following products are fed to the pond A, under regime conditions:

(1) make-up water: 1,500 t/h (to compensate the water lost in the purging and by evaporation);
(2) $CO_2$: 8.5 t/h;
(3) sodium nitrate and sodium phosphate, to maintain a concentration of 200 and 20 ppm, respectively;
(7) recycled water.

When the phototrophic microalga has matured, approximately 9,450 t/h (6) of a suspension at 0.05% by weight of microalgae in water fed to the thickening area (decanting) C, are discharged from the ponds A. The stream (5), coming from the cultivation containers B of the heterotrophic microalga, consisting of 500 t/h of a suspension at 0.5% by weight of heterotrophic micro-organisms, reaches the same thickening area.

Approximately 20% by weight is thickened in C. 36 t/h of aqueous suspension at 20% approximately by weight, are continuously removed (9) from this area, preheated in F1 to 150° C., brought to 300° C. and 12 MPa in G, fed to D and maintained under these conditions for 1 hour.

The water discharged from the thickening is respectively recycled to A, 9170 t/h by means of (7), after purging equal to 260 t/h to keep the salinity constant, and in B, 470 t/h through (8).

The biomass thermally treated in D is cooled in F1 and F2 and transported to the separator E. 2.5 t/h of bio-oil (12) are recovered from this, together with 1.5 t/h of gas and 32 t/h of an aqueous suspension (4) fed to the closed containers B of the heterotrophic microalgae, after dilution with the stream (8).

The use of the scheme, object of the present invention, allowed the specific productivity of about 20,000 ton/year of bio-oil to be reached, using an overall surface of 385 hectares and with a volume of make-up water equal to about 12,000,000 ton/year.

For the same production of bio-oil, using the technology based on phototrophic micro-organisms alone, cultivation ponds for 755 hectares and 24,000,000 ton/year of make-up water would have been necessary.

The invention claimed is:

1. An integrated process for producing a bio-oil from a phototrophic micro-organism and a heterotrophic micro-organism, the process comprising:
   a. growing at least one phototrophic microalga, in a dedicated first pond or container comprising water, nutrients, and a device adapted to distribute carbon dioxide in the water, to obtain a developed phototrophic biomass;
   b. growing at least one heterotrophic microalga, optionally in consortium with other microorganisms, in a dedicated second pond or container comprising water and nutrients, to obtain a developed heterotrophic biomass, wherein the growing is performed in the presence of carbohydrates and/or proteins transported by a suspension coming from a hydrothermal treatment of a biomass;
   c. recovering the developed phototrophic biomass and the developed heterotrophic biomass, with their growth water, as a global suspension, and thickening the global suspension at least up to 5% by weight, in a dedicated thickening section;

d. thermally treating the thickened global suspension, at a temperature in the range of 80 to 350° C. and a pressure in the range of 0.1 to 25 MPa, for at least one minute, to obtain a thermally treated thickened suspension;

e. recovering, after cooling the thermally treated thickened suspension, an oil fraction adapted to be transformed into a bio-fuel; and f. supplying a resulting aqueous suspension, rich in carbohydrates and proteins, assimilable by the heterotrophic microalgae, to (b).

2. The process according to claim 1, wherein the water in (a) and (b) is fresh or salty water, of natural or artificial origin.

3. The process according to claim 2, wherein the water is brackish water having a salt concentration in the range of 5 to 350 g/l.

4. The process according to claim 3, wherein the water is sea water or brackish water associated with a well for producing natural gas or oil.

5. The process according to claim 1, wherein the global suspension is thickened to 5 to 30% by weight in (c).

6. The process according to claim 1, wherein excess water from the thickening section is recycled both to the first pond or container, and to the second pond or container.

7. The process according to claim 1, wherein the thermal treatment is performed at a temperature in the range of 150 to 330° C., at a pressure in the range of 0.5 to 18 MPa and for 0.5 to 2 hours.

8. The process according to claim 1, wherein the thermal treatment uses energy derived from solar energy and/or from a solar pond.

9. The process according to claim 1, wherein the global suspension is thickened to 18 to 25% by weight.

10. The process according to claim 1, wherein the growing (b) is performed in consortium with at least one other microorganism.

11. The process according to claim 1, wherein the first pond or container, the second pond or container, or both the first and second ponds or containers are 5 to 100 m in length.

12. The process according to claim 1, wherein the first pond or container, the second pond or container, or both the first and second ponds or containers are 1 to 100 m in width.

13. The process according to claim 1, wherein the first pond or container, the second pond or container, or both the first and second ponds or containers are greater than 0.2 m in depth.

14. The process according to claim 1, wherein the first pond or container, the second pond or container, or both the first and second ponds or containers are 0.5 to 10 m in depth.

15. The process according to claim 1, wherein the phototrophic microalga is at least one strain belonging to at least one genus selected from the group consisting of *Tetraselmis, Nannochloropsys, Scenedesmus, Ankistrodesmus, Phaeodactylum, Chlorella, Amphipleura, Amphora, Chaetoceros, Cyclotella, Cymbella, Fragilaria, Navicula, Nitzschia, Achnantes, Dunaliella, Oscillatoria*, and *Porphiridium*.

16. The process according to claim 1, wherein the heterotrophic microalga is at least one strain belonging to at least one genus selected from the group consisting of *Chlorella, Nannochloropsys, Nitzschia*, and *Thraustochytrium*.

17. The process according to claim 10, wherein the other microorganism is at least one strain belonging to at least one genus selected from the group consisting of alpha-*Proteobacteria*, beta-*Protobacteria, Actinobacteria, Firmicutes*, and *Flavobacteria-Cytophaga*.

18. The process according to claim 1, wherein the phototrophic microalga is a phototrophic strain belonging to the genus *Nannochloropsys*.

19. The process according to claim 1, wherein the heterotrophic microalga is a heterotrophic strain belonging to the genus *Nannochloropsys*.

20. The process according to claim 1, wherein the phototrophic microalga is a phototrophic strain belonging to the genus *Nannochloropsys*, and the heterotrophic microalga is a heterotrophic strain belonging to the genus *Nannochloropsys*.

* * * * *